(12) United States Patent
Nam et al.

(10) Patent No.: US 7,824,718 B2
(45) Date of Patent: Nov. 2, 2010

(54) **EXTRACT OF *DIOSCOREA OPPOSITA* THUNB SHOWING NEURONAL CELL-PROTECTING ACTIVITY FOR TREATING MEMORY LOSS**

(75) Inventors: Sang Il Nam, Seoul (KR); Ju Hyun Park, Seoul (KR); Jin Woong Kim, Seoul (KR); Kee Dong Yoon, Seoul (KR)

(73) Assignee: Tong Yang Moolsan Co., Ltd., Seoul (KR)

( * ) Notice: Subject to any disclaimer, the term of this patent is extended or adjusted under 35 U.S.C. 154(b) by 265 days.

(21) Appl. No.: 11/915,373

(22) PCT Filed: May 23, 2006

(86) PCT No.: PCT/KR2006/001920

§ 371 (c)(1),
(2), (4) Date: Nov. 23, 2007

(87) PCT Pub. No.: WO2006/126816

PCT Pub. Date: Nov. 30, 2006

(65) Prior Publication Data

US 2009/0285910 A1    Nov. 19, 2009

(30) Foreign Application Priority Data

May 23, 2005    (KR) .................... 10-2005-0042959
Apr. 10, 2006    (KR) .................... 10-2006-0032166

(51) Int. Cl.
*A61K 36/00*    (2006.01)
(52) U.S. Cl. ...................... 424/773; 424/725
(58) Field of Classification Search ............ None
See application file for complete search history.

(56) References Cited

U.S. PATENT DOCUMENTS 5,589,154 A * 12/1996 Anderson .................. 424/1.41

FOREIGN PATENT DOCUMENTS

CN    1210722    * 3/1999

OTHER PUBLICATIONS

Chung, H. Fractionation and Quantitative Analysis of Lipid Components in Korean Yam (*Dioscorea*) Tubers; Han'guk Nonghwa Hakhoechi (1994), 37(6), 509-15.*
Medline Plus (online: URL< http://www.nlm.nih.gov/medlineplus/braindiseases.html > accessed Feb. 25, 2010, pp. 1-3).*
Medline Plus online: URL< http://www.nlm.nih.gov/medlineplus/degenerativenervediseases.html > accessed Feb. 25, 2010, pp. 1-3).*
Kermer et al. Neuronal Apoptosis in Neurodegenerative Diseases: From Basic Reasearch to Clinical Application; Neurodegenerative Diseases, 2004; 1, pp. 9-19.*

(Continued)

*Primary Examiner*—Patricia Leith
(74) *Attorney, Agent, or Firm*—Hogan Lovells US LLP (57) ABSTRACT

The present invention relates to a composition comprising an extract of *Dioscorea opposita* having neuron-protective activity for preventing and treating brain disease. The extracts from *Dioscorea opposita* show potent neuronal cell protective activity by inhibiting neuronal cell death caused by neuro-toxicity of glutamate and $H_2O_2$ therefore it can be used as the therapeutics or health food for treating and preventing brain diseases.

1 Claim, 5 Drawing Sheets

OTHER PUBLICATIONS

Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*
Plants for a Future database, online: URLhttp://www.pfaf.org/database/plants.php?Dioscorea+batatas, accessed Feb. 25, 2010, pp. 1-11.*
Chung, H. Fractionation and Quantitative Analysis of Lipid Components in Korean Yam (*Dioscorea*) Tubers; Han'guk Nonghwa Hakhoechi (1994), 37(6), 509-15, full English translation.*

Kirino T. Sano K., Acta Neuropathol., 62, pp. 201-208, 1984.
Kirino T. Brain Research, 239, pp. 57-69, 1982.
Kang T. C,, et al., J. Neurocytol., 30, pp. 945-955, 2001.
Won M. H., et al., Brain Research, 836, pp. 70-78, 1999.
Sun A. Y., Chen Y. M., J. Biomed. Sci., 5, pp. 401-414, 1998.
Zhao G. H et al., Acta Pharmaceutica Sinica, 38, pp. 37-41, 2003.
Kim et al., J. Neurosci. Res. 74, pp. 948-955, 2003.
Kim et al., Free Radic. Biol. Med., 32(7), pp. 596-604, 2002.
Kim et al., J. Neurosci. Res., 53, pp. 426-432, 1998.
Morris, J. Neurosci. Methods, 11, pp. 47-60, 1984.

* cited by examiner

EXTRACT OF *DIOSCOREA OPPOSITA* THUNB SHOWING NEURONAL CELL-PROTECTING ACTIVITY FOR TREATING MEMORY LOSS

This application is the U.S. National Phase under 35 U.S.C. §371 of International Application PCT Patent Application No. PCT/KR2006/001920, filed on May 23, 2006, which claims priority to Korean Patent Application No. 10-2005-0042959, filed on May 23, 2005, and Korean Patent Application No. 10-2006-0032166, filed on Apr. 10, 2006; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

1. Technical Field

The present invention relates to a composition comprising crude extract or non-polar solvent soluble extract of *Dioscorea opposita* having neuron-protective activity for preventing and treating brain disease.

2. Background Art

In the twentieth century, as the average life span of human has been increasing with the rapid development of life science and medicine, new social problems including increased population ratio of older people are coming to the front, especially, the chronic degenerative disease have been more rapidly increased than acute infectious diseased having been main aetiology of death for 50 years.

Among the chronic degenerative disease, a cerebrovascular disease to cause to death has become an important disease and ranked to the second frequent disease in lethal diseases to die due to single aetiology Cerebrovascular disease can be classified into two types. One is hemorrhagic brain disease mainly occurred by external impact such as traffic accident resulting in cerebral hemorrhage and another is ischemic brain disease mainly occurred by aging and other factors resulting in cerebrovascular occlusion.

In case that temporary ischemia is occurred, the supply of oxygen and glucose are blocked to cause the decrease of ATP and edema and finally those serial phenomena give rise to extensive brain damage. The death of neuronal cells appears at considerable times after the ischemia, which is called as delayed neuronal death. Through transient forebrain ischemic model experiment using by Mongolian gerbil, it is reported that there occurred the death of neuronal cell at CA1 region of hippocampus four days after the ischemia inducement (Kirino T. Sano K., *Acta Neuropathol.*, 62, pp 201-208, 1984; Kirino T. *Brain Research*, 239, pp 57-69, 1982).

There have been reported that the mechanism of neuronal cell death is classified into two types: one is excitational neuronal cell death mechanism characterized that excess amount of glutamate is accumulated in outer cell after cerebral ischemia occurred and the glutamate is flowed into inner cell apoptosis to cause to neuronal cell death due to excess accumulation of calcium ion in inner cell (Kang T. C., et al., *J. Neurocytol.*, 30, pp 945-955, 2001); another is Oxidative neuronal cell death characterized that abrupt oxygen supply causes to the increase of in vivo radical resulting in damages of cytoplasm (Won M. H., et al., *Brain Research*, 836, pp 70-78, 1999; Sun A. Y., Chen Y. M., *J. Biomed. Sci.*, 5, pp 401-414, 1998; Flowers F, Zimmerman J. *J. New Horiz.*, 6, pp 169-180, 1998)

There have been studied and developed to search effective substance effectively inhibiting neuronal cell death and the action mechanism of the substance till now, however, there has not yet reported the substance to inhibit neuronal cell death effectively. There have been several attempts to find effective agent till now. For example, t-PA (tissue Plasminogen activator), sole FDA approved treating agent for ischemia, has thrombolytic activity which can dissolve blood thrombus to induce rapid supply of oxygen and glucose. However, it has several disadvantages such as necessity to instant use, the occurrence of hemorrhagic cerebrovascular disease caused by thinned blood vessel wall in case of excessive or frequent use of the agent. MK-801, a calcium channel blocker inhibit initial calcium influx effectively, however, the further development was postponed because of its adverse effect.

*Dioscorea opposita* Thunb(=*Dioscorea batatas* Decne.) belonged to Dioscoreacea, is originally grown in China. It is also distributed or cultivated in Korea and Japan. The rhizome of *Dioscorea opposita* has been used to an edible and traditional medicinal plant in Korea. It has been reported that *D. opposita* containing allantoin, diosgenin, dioscine, dopamine, ergosterol and so on (Nie G. H, et al; *Chinese Traditional Herbal Drugs*, 24, pp 158-160, 1993; Zhao G. H, et al; *Acta Pharmaceutica Sinica*, 38, pp 37-41, 2003) and used for treating of anorexia, chronic diarrhea, asthma, dry coughs, oligunia, diabetes and so on. However, there has been not reported or disclosed about therapeutic effect for brain disease of *Dioscorea opposita* in any of above cited literatures, the disclosures of which are incorporated herein by reference.

Accordingly, the present inventors have discovered that the extract of *Dioscorea opposita* shows neuronal cell-protective activity by inhibiting neuronal cell death and have finally completed the present invention.

These and other objects of the present invention will become apparent from the detailed disclosure of the present invention provided hereinafter.

DISCLOSURE OF THE INVENTION

Technical Problem

Accordingly there have been urgently needed to find effective substances providing with verified efficacy as well as low or at least toxicity from natural resource till now.

Technical Solution

Accordingly, it is an object of the present invention to provide a composition comprising the crude extract or non-polar solvent soluble extract of *Dioscorea opposita* as an active ingredients for the treatment and prevention of brain disease.

The term "crude extract" disclosed herein comprises the extract prepared by extracting plant material with water, lower alcohols such as methanol, ethanol, preferably methanol and the like, or the mixtures thereof.

The term "polar solvent soluble extract" disclosed herein can be prepared by extracting the above described crude extract with polar solvent, for example, water, lower alcohol such as methanol, ethanol, preferably butanol and the like, or the mixtures thereof.

The term "non-polar solvent soluble extract" disclosed herein can be prepared by extracting the above described crude extract with non-polar solvent, for example, hexane, ethyl acetate or chloroform, preferably chloroform.

The term "*Dioscorea opposita*" disclosed herein comprises a natural, cultivated and cell-cultured plant preferably the plant cultivated by the procedure disclosed in the published Korean patent No. 10-2005-279 comprising the step for producing a good seed; the large amount of the excellent stem cuttings is proliferated by culturing growing point and virus inspection of *Dioscorea opposita* Thunb and then the stem cuttings prepared by tree cutting method is transferred to the field to be acclimated thereto or subjected to tissue culture in Petri dish to produce microtuber. The upper part of the transferred stem cuttings is grown by providing appropriate amount nutrient to afford a germ-free seed.

In accordance with another aspect of the present invention, there is also provided a use of crude extract or non-polar solvent soluble extract of *Dioscorea opposita* for manufacture of medicines employed for treating or preventing brain disease by protecting neuronal cell.

In accordance with another aspect of the present invention, there is also provided a method of treating or preventing brain disease in mammals by protecting neuronal cell, wherein the method comprises administering a therapeutically effective amount of crude extract or non-polar solvent soluble extract of *Dioscorea opposita* into the mammal suffering with brain disease.

An inventive extract isolated from *Dioscorea opposita* may be prepared in accordance with the following preferred embodiment.

Hereinafter, the present invention is described in detail.

For example, at the $1^{st}$ step, *Dioscorea opposita* could be prepared by the procedure disclosed in the published Korean Patent No. 10-2005-279 comprising the step for producing a good seed; i.e. the large amount of the excellent stem cuttings is proliferated by culturing growing point and virus inspection of *Dioscorea opposita* Thunb and then the stem cuttings prepared by tree cutting method is transferred to the field to be acclimated thereto or subjected to tissue culture in Petri dish to produce microtuber. The upper part of the transferred stem cuttings is grown by providing appropriate amount nutrient to afford a germ-free seed.

At the $2^{nd}$ step, the rhizome of *D. opposita* prepared in step 1, is dried, cut, crushed and mixed with 1 to 20-fold, preferably, approximately 3 to 10 fold volume of distilled water, lower alcohols such as methanol, ethanol, butanol and the like, or the mixtures thereof, preferably water of methanol; the solution is treated with hot water at the temperature ranging from 20 to 100° C., preferably from 50 to 100° C., for the period ranging from 1 hour to 10 days, preferably approximately from 2 to 5 hours with extraction method by the extraction with hot water, cold water, reflux extraction, or ultra-sonication extraction, consecutively; the residue is filtered and then dried by vacuum freeze-drying to obtain dried crude extract powder of *Dioscorea opposita* which can be soluble in water, lower alcohols, or the mixtures thereof.

At the $3^{rd}$ step, the crude extract prepared by above step, is suspended in water, and then is mixed with non polar solvent such as hexane, chloroform, ethyl acetate and the like to treatment the crude extract; the non-polar solvent soluble layer is collected to obtain non-polar solvent soluble extract of the present invention.

At the $4^{th}$ step, the remaining polar solvent soluble layer is collected to obtain polar solvent soluble extract of the present invention which is soluble in water, lower alcohols such as butanol, or the mixtures thereof.

In accordance with another aspect of the present invention, there is provided a pharmaceutical composition comprising the crude extract or non-polar solvent soluble extract of *Dioscorea opposita* prepared by above preparation method for the treatment and prevention of brain disease by protecting neuronal cell as active ingredients.

In accordance with another aspect of the present invention, there is also provided a use of crude extract or non-polar solvent soluble extract of *Dioscorea opposita* prepared by above preparation method for manufacture of medicines employed for treating or preventing brain disease by protecting neuronal cell.

In accordance with another aspect of the present invention, there is also provided a method of treating or preventing brain disease by protecting neuronal cell, wherein the method comprises administering a therapeutically effective amount of crude extract or non-polar solvent soluble extract of *Dioscorea opposita* prepared by above preparation method.

The inventive composition for treating and preventing brain disease by protecting neuronal cell may comprises above extracts as 0.1~20% by weight based on the total weight of the composition.

Above described brain disease comprises stroke, Alzheimer's disease (AD), Parkinson's disease (PD), sentil dementia and the like.

The inventive composition may additionally comprise conventional carrier, adjuvants or diluents in accordance with a using method well known in the art. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging from 0.00001 to 100 mg/kg, preferably, 0.001 to 100 mg/kg by weight/day of the inventive extract of the present invention. The dose may be administered in single or divided into several times per day.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

Also, the present invention provides a composition of the health food and beverage for the prevention and improvement of brain disease by protecting neuronal cell.

To develop for health food, examples of addable food comprising the above extracts of the present invention are various food, beverage, gum, vitamin complex, health improving food and the like, and can be used as powder, granule, tablet, chewing tablet, capsule or beverage etc.

The above described composition therein can be added to food, additive or beverage, wherein, the amount of the above described extract in food or beverage may generally range from about 0.01 to 80 w/w %, preferably 0.01 to 15 w/w % of total weight of food for the health food composition and 0.02 to 5 g, preferably 0.3 to 1 g on the ratio of 100 ml of the health beverage composition.

Providing that the health beverage composition of present invention contains above described extract as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

Inventive extract of the present invention has no toxicity and adverse effect therefore they can be used with safe.

It will be apparent to those skilled in the art that various modifications and variations can be made in the compositions, use and preparations of the present invention without departing from the spirit or scope of the invention.

Advantageous Effects

The present invention provides a composition comprising a crude extract or non-polar solvent soluble extract of *Dioscorea opposita* as an active ingredient in an effective amount to treat and prevent brain disease by protecting neuronal cell.

BRIEF DESCRIPTION OF THE DRAWINGS

The above and other objects, features and other advantages of the present invention will more clearly understood from the following detailed description taken in conjunction with the accompanying drawings, in which;

FIGS. 3 A, B, C and D represent the neuroprotective effect of *D. opposita* on scopolamine-induced amnesic mice in trial 1 and 2 of the Morris water maze test.

FIGS. 4 A, B and C represent the results of a probe trial (120 s) in which there was no platform present.

BEST MODE FOR CARRYING OUT THE INVENTION

It will be apparent to those skilled in the art that various modification and variation can be made in the compositions, use and preparations of the present invention without departing from the spirit or scope of the invention.

The present invention is more specifically explained by the following examples. However, it should be understood that the present invention is not limited to these examples in any manner.

Mode for the Invention

The present invention is more specifically explained by the following examples. However, is should be understood that the present invention is not limited to these examples in any manner.

The following Reference Example, Examples and Experimental Examples are intended to further illustrate the present invention without limiting its scope.

Example 1

1-1. The Cultivation of *Dioscorea opposita* Thunb

The "*Dioscorea opposita* Thunb" purchased from Tong Yang Moolsan Co., Ltd located in Yong-in city cultivated and cell-cultured plant root prepared by the procedure disclosed in already published Korean Patent No. 10-2005-279 comprising the step for producing a large amount of the excellent stem cuttings is proliferated by culturing growing point and virus inspection of *Dioscorea opposita* Thunb and then the stem cuttings prepared by tree cutting method is transferred to the field to be acclimated thereto or subjected to tissue culture in Petri dish to produce microtuber. The upper part of the transferred stem cuttings is grown by providing appropriate amount of nutrients.

1-2. Preparation of the Crude Extract of the Rhizomes of *D. opposita*

160 g of dried the above the rhizomes of *Dioscorea opposita* prepared by Example 1-1 and cut into small pieces, mixed with 1.6 L of 80% methanol and the mixture was subjected to sonication extraction with sonicator (Branson Co. U.S.A.), extracted by cool-water three times. The extract was filtered with filter paper to remove the debris.

The filtrate was pooled and concentrated by rotary evaporator (N-1000, Eyela Co. Japan) at 55~65° C. under reduced pressure and dried with freezing dryer (Speed Spec 3000, Bio-Rad Co. U.S.A.) to obtain 14 g of dried crude extract.

1-3. Preparation of Non-Polar Solvent Soluble Extract 1-3-1. Preparation of n-Hexane Soluble Fraction 500 ml of distilled water was added to 14 g of the crude extract obtained in Example 1-2. 500 ml of n-hexane was added thereto in separatory funnel, shaken vigorously to divide into n-Hexane soluble layer and water soluble layer.

The above water soluble layer was mixed with equivalent amount of n-Hexane and then divided into n-hexane soluble layer and water soluble layer. The fractionation process was repeated 3 times.

The above n-hexane soluble layer was concentrated by rotary evaporator, dried with freeze dryer to obtain 40.6 mg of n-hexane soluble extract.

1-3-2. Preparation of Chloroform Soluble Fraction

The upper layer prepared from Example 1-3-1, was mixed with chloroform and then divided into chloroform soluble layer and water soluble layer. The fractionation process was repeated 3 times.

Above chloroform soluble layer was concentrated by rotary evaporator, dried with freeze dryer to obtain 134.9 mg of chloroform soluble extract.

1-3-3. Preparation of Ethyl Acetate Soluble Fraction

The upper layer prepared from Example 1-3-2, was mixed with ethyl acetate and then divided into ethyl acetate soluble layer and water soluble layer. The fractionation process was repeated 3 times.

Above ethyl acetate soluble layer was concentrated by rotary evaporator, dried with freeze dryer to obtain 30.9 mg of ethyl acetated soluble extract.

1-3-4. Preparation of n-Butanol Soluble Fraction

Remaining water soluble layer in Example 1-3-3 was fractionated with butanol and finally, 679.9 mg of a butanol soluble extract was obtained to use as a test sample in the following experiments.

Reference Example 1

1-1. Preparation of Samples

The non-polar solvent soluble extract prepared in Example 1-3 was suspended in DMSO (Sigma Co., Ltd) as a final concentration of >0.1%. Each suspension was filtered with 0.2 μm membrane filter (Millipore Co., Ltd.) to remove bacteria etc and used in following experiment.

1-2. Animals

Sprague-Dawley mice weighing 250-260 g were obtained from Experimental Animal Breeding Center of Seoul National University (Seoul, Korea) and bred under a 12:12 h light-dark cycle. The temperature was constant at 22° C. with freely accessible test water and food. All animal experiments were done according to the guideline of the Committee on Care and Use of Laboratory Animals of the Seoul National University.

1-3. Drug

The sample was obtained from the chloroform fraction of *D. opposita* extract. Scopolamine an antagonist of muscarinic receptor was used as a positive control. In the study, scopolamine was dissolved in physiological saline and then subcutaneously injected at the dose of 1 mg/kg per body weight. The each of *D. opposita* was injected into the mice by suspending in a 0.5% carboxymethylcellulose (CMC)-saline solution according to the desired concentration i.e. 5 and 20 mg/ml for doses of 50 and 200 mg/kg per body weight, respectively. 0.5% CMC-saline was injected to animals as a negative control.

1-4. Statistical Analysis

Each data is presented as the mean±S.D. The potency in vitro assay is shown as relative protection (%) whereas the latency time of Morris water maze test and passive avoidance latency time test were analyzed according to two-way ANOVA and one-way ANOVA program respectively. The data were considered as significant statistically when the probability shows 0.05 or less.

Experimental Example 1

Neuroprotective Activity of the Extract of *Dioscorea opposita*

To investigate the protecting activity of test samples prepared in Examples against damaged brain cortical cell caused by glutamate and $H_2O_2$ radical, following experiment was performed according to the procedure disclosed in the published reference (Kim et al., *J. Neurosci. Res.* 74, pp 948-955, 2003; Kim et al., *Free Radic. Biol. Med.*, 32(7), pp 596-604, 2002).

1-1. Isolation and Culture of Rat Cortical Cell

After delivering cerebrum from white fetal rat, the encephalomening membrane of cerebrum was removed carefully by using microscopy. The isolated cerebrum tissue was treated with 0.25% Trypsin for 30 mins to soften the tissue in order to each tissue was separated and cultivated according to the procedure disclosed in the literature ((Kim et al., *J. Neurosci. Res.*, 53, pp 426-432, 1998).

The cerebral cortex cells mixed with neurons and non-neuronal cells were isolated from 17- to 19-day-old fetal Sprague-Dawley rats and then subjected to primary culture. In brief, the cerebral cortex cells were plated on 48-well culture plates coated with collagen at the cell density of $1 \times 10^6$ cell/ml and cultivated with Dulbecco's modified Eagle's medium (DMEM) containing 10% heat-inactivated fetal calf serum, 10% penicillin, and 100 μg/ml streptomycin at 37° C.

in a humidified atmosphere of 95% air—5% $CO_2$. Cytosine-$\beta$-$_D$-arbinofuranoside (1 μM) was added to the culture medium 3 days after the plating to inhibit the proliferation of non-neuronal cells. After 15 days, the cultured cells were used for following experiments.

1-2. Sample Treatment

The extracts of *Dioscorea opposita* were suspended in DMSO (Sigma Co., Ltd) and diluted to the extent that the final concentration reaches to <0.1%. Each suspension was filtered with 0.22 μm membrane filter (Millipore Co., Ltd.) to sterilize. After the concentrations of each fractions were adjusted to 100 μg/ml and 10 μg/ml, The test samples with various final concentration of various fractions were named as follows: 100 μg/ml of hexane layer (H100), 10 μg/ml of hexane layer (H10), 100 μg/ml of water layer (W100), 10 μg/ml of water layer (W10), 100 μg/ml of ethyl-acetate layer (E100), 10 μg/ml of ethylacetate layer (E10), 100 μg/ml of chloroform layer (C100), 10 μg/ml of chloroform layer (C10), 100 μg/ml of butanol layer (B100), 10 μg/ml of butanol layer (B10) respectively. The cultured cell was pretreated with each test sample 1 hour before the glutamate treatment and the protective activity of *D. opposita* against the death of cerebral cortex cells was assessed.

1-3. Cell Protective Activity Against Glutamate Induced-Neurotoxicity

The tested fractions were dissolved in DMSO and diluted to the extent that the final concentration reaches to <0.1%. The matured cerebral cortex cells for 15 days were pretreated with the test fractions for 1 hour and then exposed to 100 μM glutamate. After further incubation for 24 hour, the neuronal survival was quantified using by MTT assay, which yields blue formazan products in living cells. Data was expressed as the relative protection (%), which was calculated as 100× [Optical density (OD) of sample-treated cells–OD of glutamate-treated cells]/[OD of control cells-OD of glutamate-treated cells].

1-4. Cell Protective Activity Against $H_2O_2$ Induced-Neurotoxicity

The cells were pretreated with various concentrations of test samples, i.e., 1, 10, 50, 100 μg/ml, for 1 hour and then exposed to 100 μM $H_2O_2$. After additional incubation for 24 hours, the cell viability in the cultures was assessed by MTT assay, which reflects on enzymatic function of mitochondrial cells. Data was also expressed as the relative protection (%), which was calculated as 100×[Optical density (OD) of sample-treated cells-OD of $H_2O_2$-treated cells]/[OD of control cells–OD of $H_2O_2$-treated cells]

1-5. MTT assay

After 24 hour's treatment with glutamate and $H_2O_2$, 2 mg/ml of MTT solution was added to the cell to the extent the final concentration of the medium reaches 1% and the medium was further incubated for 2 hours. The formed formazan was dissolved in 300 ml of DMSO to dissolve crystals and the absorbance was measured at 560 nm by microplate reader (ELISA reader, Molecular devices Co., U.S.A.) to calculate the cell viability (Kim et al., *J. Neurosci. Res.*, 53, pp 426-432, 1998).

1-6. Results 1-6-1. Neuroprotective Activity of Non-Polar Solvent Soluble Extracts As a result of assessing neuroprotective activity of each non-polar solvent soluble extracts of *D. opposita*, chloroform soluble extract increased the cell viability significantly by inhibiting neuronal cell death caused by glutamate induced-neurotoxicity (See Table 1)

TABLE 1

| | | Protection activity (%) | Standard deviation | Reliability |
|---|---|---|---|---|
| Control | | 100 | 3.7 | |
| Glutamate-injured | | 0 | 4.8 | |
| MK801 | | 79 | 8.5 | ** |
| Hexane | H100 | 43.7 | 9.9 | * |
| | H10 | 51.7 | 6.3 | ** |
| $CHCl_3$ | C100 | 80.1 | 10.8 | * |
| | C10 | 26.1 | 2.8 | * |
| EtOAc | E100 | 61.2 | 11.1 | * |
| | E10 | 18.9 | 1.4 | * |
| BuOH | B100 | 33.5 | 6 | * |
| | B10 | 18.8 | 8.3 | |
| Water | W100 | 52.6 | 7.9 | * |
| | W10 | 9.9 | 3.7 | |

* Values shown are the means ± S.D. (3 cultures per experiment).
* Cell viabilities of control and glutamate-treated cells were representative as 100% and 0%, respectively.
* Glutamate-injured cells differ significantly from the control at a level of $p < 0.01$ **
* MK-801, a non-competitive antagonist of the NMDA receptor differ significantly from the glutamate injured cell at a level of $p < 0.01$ **
* Means value is significantly different (* $p < 0.05$, ** $p < 0.01$) from the value of the glutamate treated cells.

1-6-2. The Effect of *D. opposita* Extract on Neurotoxicity Induced by Glutamate The effect of *D. opposita* on glutamate-induced neurotoxicity in primary cultures of rat cortical neurons was evaluated. The glutamate-induced neurotoxicity was significantly reduced by the addition of positive control, MK-801, at the concentration of 10 μM (Relative protection=80.6±1.6%, P<0.0001). Pretreatment with *D. opposita* extract significantly increased cell viability in a dose dependent manner.

Figure 1:
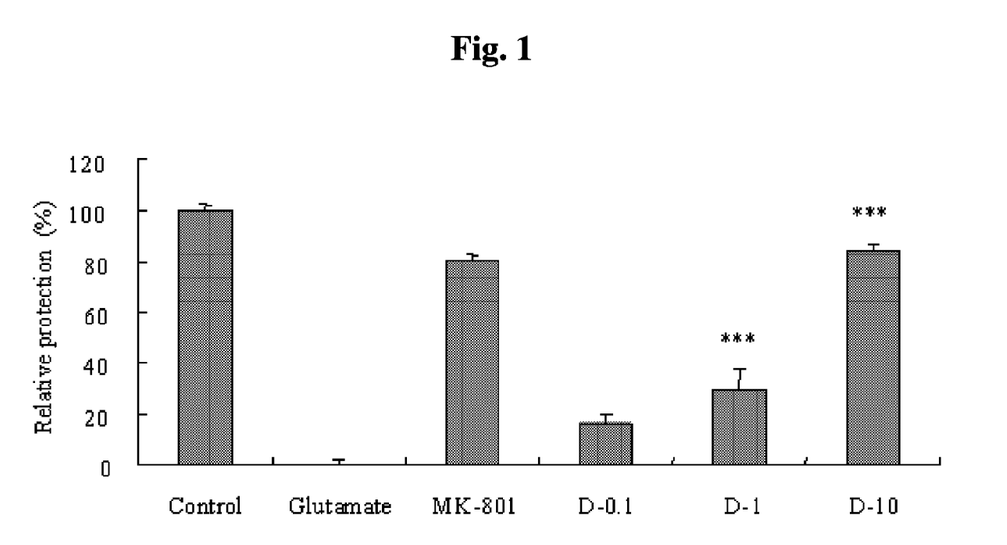
FIG. 1 shows the neuroprotective effect of *D. opposita* extract on the glutamate-induced neurotoxicity in primary cultures from rat cerebral cortex.

The result was shown that the neuronal cell was protected by the addition of chloroform soluble fraction of *D. opposita* at the concentration of 0.1, 1, 10 μg/ml in a dose dependent manner. Especially, maximum neuro-protection was obtained by the pre-treatment with 10 μg/ml of *D. opposita* extract (Relative protection=83.7±3.0%, P<0.0001) (See FIG. 1.)

1-6-3. The Effect of *D. opposita* Extract on Neurotoxicity Induced by $H_2O_2$

Figure 2:
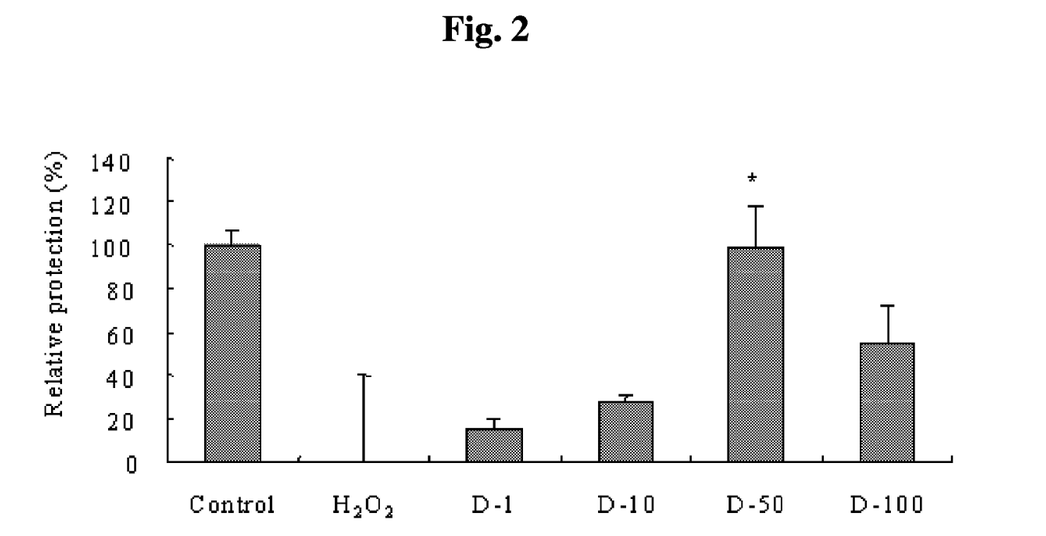
FIG. 2 shows the neuroprotective effect of *D. opposita* extract on the $H_2O_2$-induced neurotoxicity in primary cultures from rat cerebral cortex.

The effect of *D. opposita* on 200 μM of $H_2O_2$-induced neurotoxicity in primary cultures of rat cortical neurons was evaluated. The result was shown that the neuronal cell was protected by chloroform fraction of *D. opposita* at the concentration of 1, 10, 50 μg/ml dose-dependently. Especially, maximum neuro-protection was obtained by the pre-treatment with 50 μg/ml of *D. opposita* extract (Relative protection=98.8%, P<0.05)(See FIG. 2.).

Accordingly, it has been confirmed that the extract of *D. opposita* significantly protects from neuronal cell death caused by glutamate and $H_2O_2$ induced neuro-toxicity.

Experimental Example 2

The Improving Effect of *Dioscorea opposite* on Brain Function and Memory Dysfunction 2-1. Morris Water Maze Test To investigate the improving effect of the extracts of *D. opposita* on memory dysfunction, following water maze test was performed according to the method disclosed in the literature (R. Morris, *J. Neurosci. Methods*, 11, pp 47-60, 1984).

Figure 3:
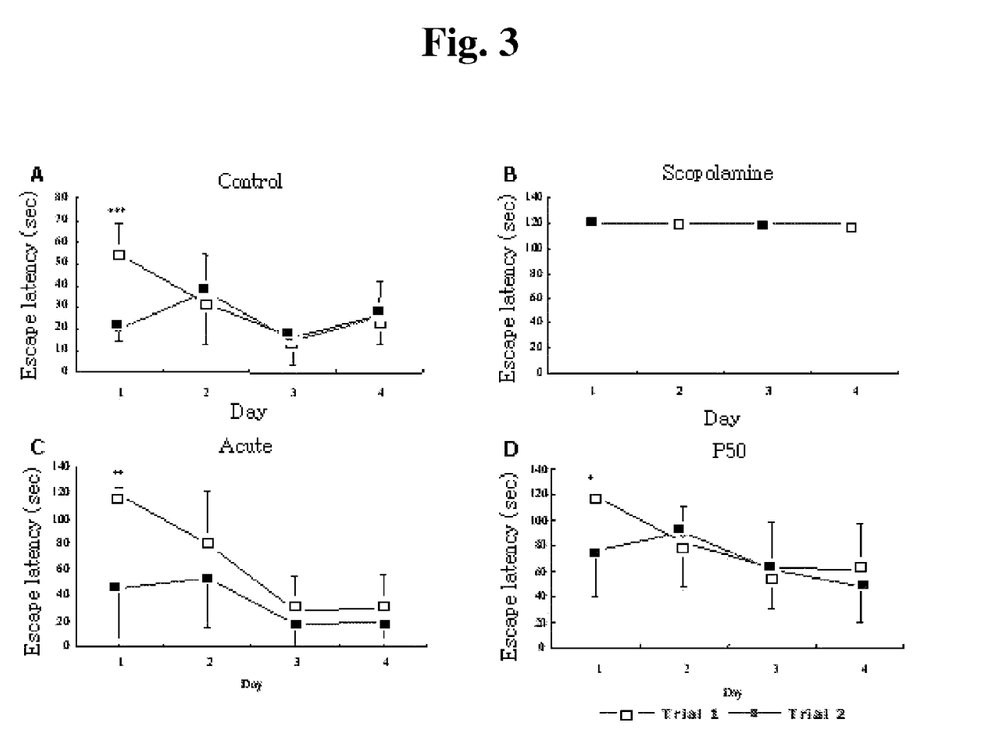

The neuro-protective effects of *D. opposita* on the escape latency (sec) taken to reach the submerged platform are illustrated in FIG. 3. The saline-treated control group mice rapidly learned the location of the submerged platform and also showed a marked reduction in escape latencies from $1^{st}$ day to $3^{rd}$ day on $1^{st}$ trial. Additionally, the result showed significant decrease of latency time from first to second trials on day 1 (FIG. 3a). In contrast, the escape latencies in trials 1 and 2 were almost unchanged throughout the four day's testing period in scopolamine-treated mice at the dose of 1 mg/kg (FIG. 3b).

The escape latencies of negative control group, scopolamine treatment group and short-term treatment group with test sample (Acute group) showed potent activity with respect to each day (F (3, 72)=23.4, P<0.0001), treatment (F (2, 72)=159.6, P<0.0001), and day-by-treatment interaction (F (6, 72)=10.1, P<0.0001) as shown in FIG. 3c. All the procedure was similar to the above-described method excepting substituting short-term treatment group with test sample with long-term treatment group (P-50 group), which had been pretreated with the extract of *D. opposita* at the dose of 50 mg/kg of liver weight for 10 days everyday, which. The escape latencies of negative control group, scopolamine treatment group and P-50 treatment group showed potent activity with respect to each Day (F (3, 72)=11.3, P<0.0001), Treatment (F (2, 72)=145.5, P<0.0001), and Day and Treatment interaction (F (6, 72)=3.5, P<0.01). Throughout the consecutive 4 day's training period, both of short-term and long-term treatment group showed gradual reduction in required time to reach the platform compared with those in mice given scopolamine alone As a result, it has been confirmed that *D. opposita* significantly antagonized the deficit in spatial memory induced by scopolamine on escape latencies in both trials. Especially, short-term test sample treatment group more shortened the escape latencies in each daily trial compared with long-term test sample treatment group.

2-1-1. Examination of the Spatial Working Memory

Figure 4:
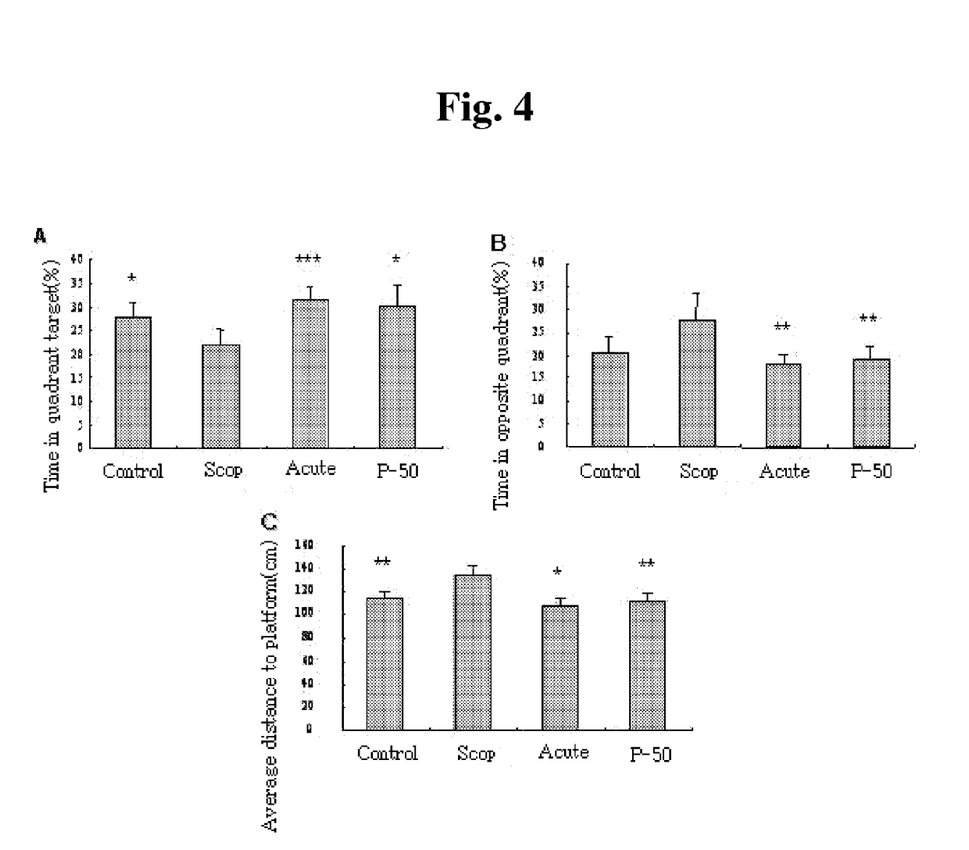

To examine the spatial working memory of mice, the platform was removed and various factors, i.e. the time that the mice spent in the target quadrant of the former platform position, the time spent in the opposite quadrant of the former platform position and average distance to the platform etc. were measured. As can be seen in FIG. 4, both of short-term and long term test sample pretreated mice (Acute and P-50 group) significantly increased the swimming time in the target quadrant of the pool where the platform was previously placed (Acute group; P<0.0001 and P-50 group; P<0.01) (FIG. 4a) whereas both of Acute and P-50 group showed significant reduction with respect to the time spent in the opposite quadrant of the former platform position (Acute group; P<0.001 and P-50 group; P<0.001) (FIG. 4b) and average distance to the platform (Acute group; P<0.01 and P-50 group; P<0.001) (FIG. 4c).

2-2. Passive Avoidance Test 2-2-1. Methods

For passive avoidance test, chloroform soluble extract was administered to the mice prior to scopolamine-induced amnesia.

An automated system with a shuttle box was used to evaluate the effects on learning memory associated with neuronal cell growth and the avoidance shuttle box (20×20×20 cm, Gemini Co., U.S.A.) was divided into two chambers of equal size having a grid with 3 mm of thickness in interval of 0.5 cm on the floor of the box. A light chamber is equipped with an illuminator. The mice were initially placed in the light chamber.

Scopolamine was injected intraperitoneally to the mouse. 30 minutes after, acquisition training was carried out, which delivering the electrical foot shock (0.5 mA, 2 s) to the mouse through the grid floor when the mouse preferring darkness went out from light chamber and entered the dark chamber.

24 hours after the acquisition trial, the identical experiment to the above-described method was repeated to measure the latency time staying at the light chamber. The data was regarded as the index which meant the memory on previous training by electronic shock. Latency to enter the dark compartment was measured for 180 sec. If it did not enter the dark chamber within the cut-off time (180 sec), it was assigned a value of 180 sec as its latency.

2-2-2. Results

Figure 5:
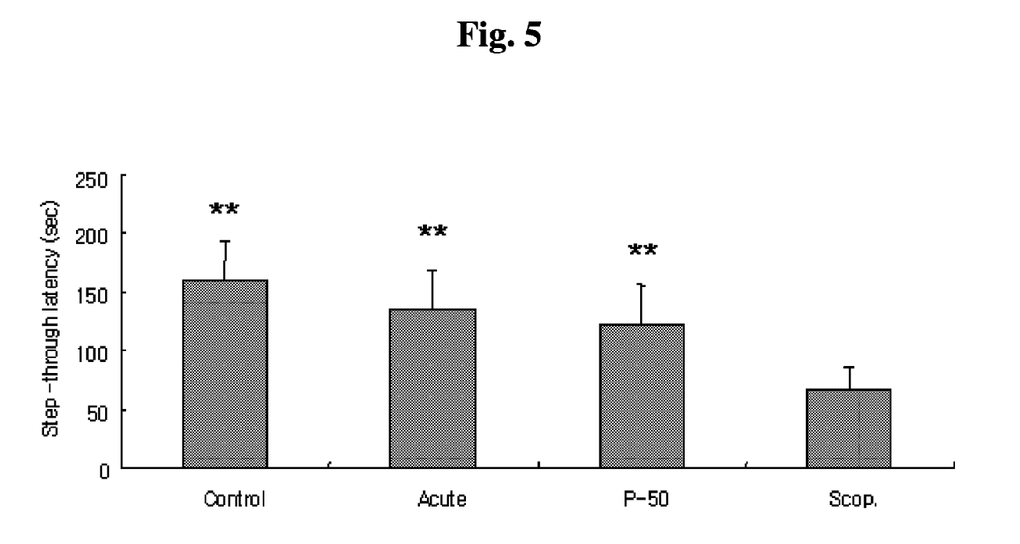
FIG. 5 presents the neuroprotective effect of *D. opposita* extract in the passive avoidance test.

As shown in FIG. 5, since the latency time in scopolamine-induced amnesia mouse was the shortest among the groups, the protection rate of scopolamine-treated group was regarded as 0% while the protection rate of CMC-saline-treated control group as 100%. The latency time of short term and long term treatment group of chloroform fraction of *D. opposita* showed 135.3±34.2 (P<0.001) and 120.7±35.2 (P<0.001) respectively.

It has been conformed that the chloroform soluble extract of *D. opposita* may significantly improve memory and recognition ability (protection rate: Acute group=71.4±38.6% (P<0.01), P-50 group=54.9±39.7% (P<0.05))

Experimental Example 3

Toxicity Test 3-1. Methods

The acute toxicity tests on ICR mice (mean body weight 25±5 g) and Sprague-Dawley rats (235±10 g, Biogenomics Co., Ltd.) were performed using by the extract of *D. opposita*. Four group consisting of 3 mice or rats was administrated orally with 10 mg/kg, 100 mg/kg and 1000 mg/kg of test sample or solvents (0.2 ml, i.p.) respectively and observed for 2 weeks.

3-2. Results

There were no treatment-related effects on mortality, clinical signs, body weight changes and gross findings in any group or either gender. These results suggested that the extract prepared in the present invention were potent and safe.

Hereinafter, the formulating methods and kinds of excipients will be described, but the present invention is not limited to them. The representative preparation examples were described as follows.

Preparation of Powder

| | |
|---|---|
| Dried powder of Example 1 | 50 mg |
| Lactose | 100 mg |
| Talc | 10 mg |

Powder preparation was prepared by mixing above components and filling sealed package.

Preparation of Tablet

| Dried powder of Example 1 | 50 mg |
|---|---|
| Corn Starch | 100 mg |
| Lactose | 100 mg |
| Magnesium Stearate | 2 mg |

Tablet preparation was prepared by mixing above components and entabletting.

Preparation of Capsule

| Dried powder of Example 1 | 50 mg |
|---|---|
| Corn starch | 100 mg |
| Lactose | 100 mg |
| Magnesium Stearate | 2 mg |

Tablet preparation was prepared by mixing above components and filling gelatin capsule by conventional gelatin preparation method.

Preparation of Injection

| Dried powder of Example 1 | 50 mg |
|---|---|
| Distilled water for injection | optimum amount |
| pH controller | optimum amount |

Injection preparation was prepared by dissolving active component, controlling pH to about 7.5 and then filling all the components in 2 ml ample and sterilizing by conventional injection preparation method.

Preparation of Liquid

| Dried powder of Example 1 | 0.1~80 g |
|---|---|
| Sugar | 5~10 g |
| Citric acid | 0.05~0.3% |
| Caramel | 0.005~0.02% |
| Vitamin C | 0.1~1% |
| Distilled water | 79~94% |
| $CO_2$ gas | 0.5~0.82% |

Liquid preparation was prepared by dissolving active component, filling all the components and sterilizing by conventional liquid preparation method.

Preparation of Health Food

| Extract of Example 1 | 1000 mg |
|---|---|
| Vitamin mixture | optimum amount |
| Vitamin A acetate | 70 μg |
| Vitamin E | 1.0 mg |
| Vitamin $B_1$ | 0.13 mg |
| Vitamin $B_2$ | 0.15 mg |
| Vitamin B6 | 0.5 mg |
| Vitamin B12 | 0.2 μg |
| Vitamin C | 10 mg |
| Biotin | 10 μg |
| Amide nicotinic acid | 1.7 mg |

-continued

| Folic acid | 50 μg |
|---|---|
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above-mentioned vitamin and mineral mixture may be varied in many ways. Such variations are not to be regarded as a departure from the spirit and scope of the present invention.

Preparation of Health Beverage

| Extract of Example 1 | 1000 mg |
|---|---|
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the crude extract and non-polar soluble extract of *Dioscorea opposita* show neuronal cell-protective activity effects by inhibiting neuronal cell death, and increase cell viability reduced by glutamate treatment, therefore, it can be used as the therapeutics or health food for treating and preventing brain diseases in which are caused by neuronal cell death.

What is claimed is:

1. A pharmaceutical composition for treating degenerative memory loss, wherein said composition comprises an effective amount of a *Dioscorea oppositae* extract, wherein said extract is prepared by
   (a) extracting rhizomes of *Dioscorea oppositae* with a solvent selected from the group consisting of water, lower-alcohol and mixtures thereof; and filtering to collect a first extract,
   (b) partitioning said first extract between n-hexane and water and collecting the water layer, and
   (c) mixing said water layer of part (b) with chloroform and collecting the chloroform-soluble layer, whereby the chloroform-soluble layer is the extract.

* * * * *